United States Patent [19]

Schinhammer

[11] 4,094,068

[45] June 13, 1978

[54] ORTHODONTIC BRACKET ASSEMBLY

[75] Inventor: Karl Schinhammer, Iserlohn-Letmathe, Germany

[73] Assignee: Scheu-Dental Inh. Rudolf Scheu Herstellung & Vertrieb Von Dentalbedarf, Letmathe, Germany

[21] Appl. No.: 705,898

[22] Filed: Jul. 16, 1976

[30] Foreign Application Priority Data

Aug. 1, 1975 Germany ............................ 2534368

[51] Int. Cl.$^2$ ............................................. A61C 7/00

[52] U.S. Cl. ............................................. 32/14 A

[58] Field of Search ..................................... 32/14 A

[56] References Cited

U.S. PATENT DOCUMENTS

| | | | |
|---|---|---|---|
| 3,345,745 | 10/1967 | Muller | 32/14 A |
| 3,504,438 | 4/1970 | Wittman et al. | 32/14 A |
| 3,738,005 | 6/1973 | Cohen | 32/14 B |
| 3,765,091 | 10/1973 | Northcutt | 32/14 A |
| 3,797,115 | 3/1974 | Silverman | 32/14 A |

*Primary Examiner*—Robert Peshock
*Attorney, Agent, or Firm*—Toren, McGeady and Stanger

[57] ABSTRACT

An orthodontic bracket assembly including brackets mounted upon teeth to effect orthodontic treatment thereof is provided with a self adhesive layer adhered on one side thereof to the surface of the orthodontic bracket which is used to fasten the bracket upon a tooth. A protective foil is arranged to extend on one side of bracket wings formed upon the orthodontic bracket and defining a slot adapted to receive therein a regulating arch when the brackets are mounted upon teeth to be treated. The protective foil defines a gap or spacing within which the base of the orthodontic bracket extends and within which liquid adhesive may be introduced for attaching the bracket to the teeth to be treated.

11 Claims, 8 Drawing Figures

ORTHODONTIC BRACKET ASSEMBLY

BACKGROUND OF THE INVENTION

The present invention relates generally to orthodontic devices and more particularly to an assembly for orthodontic brackets applied to teeth which are to be orthodontically treated. The type of bracket involved with the invention includes a base which is secured to a respective tooth and bracket wings which extend laterally on both sides of the brackets and which define therebetween a central slot adapted to receive therein a regulating arch. The invention also relates to a method for preparation in the laboratory of the bracket assembly and for application of the bracket to a tooth.

Brackets of the type to which the present invention relates have been heretofore temporarily secured upon a positive jaw model in proper position for regulation. An elastic mold negative or transfer matrix is then produced to receive the brackets and by means of this matrix the brackets are transferred to teeth in the mouth and are cemented thereupon.

The materials for forming the transfer matrix have generally been composed of soft rubber materials having a modulus of elasticity of between about 700 to 1000 $kg/cm^2$ and a wall thickness of between about 2 to 4 mm. These characteristics are related mainly to providing the transfer matrix with an ability to be detached from the orthodontic device after the bracket is cemented in the mouth inasmuch as the matrix material will usually extend beneath the bracket wings and it can be easily detached with provision of an appropriate or corresponding elasticity of the matrix material. Such soft elastic matrix material usually requires a considerable wall thickness in order to obtain a sufficient stability of form. Furthermore, the transfer matrix must extend sufficiently far over the teeth and into the range of the gums. This is generally an unfavorable characteristic inasmuch as the gums are subject to constant change and there may thus be caused incorrectness in the application of the bracket when the matrix is later applied in the mouth. Additionally, when the transfer matrices are applied upon the teeth, squeezing of the adhesive in the mouth is unavoidable. In a particularly unfavorable situation, adhesive may even flow into the interdental spaces thereby leading to blockage between the teeth and making the regulating forces of the orthodontic apparatus ineffective. Furthermore, uncontrollable excess adhesive may be formed under the projecting transfer matrices on the teeth outside of the bracket base thereby causing difficulty and time-consuming procedures when removal is necessary after hardening.

Furthermore, metal brackets with perforated bases have the disadvantage that the material of the transfer matrix tends to penetrate into these perforations. The transfer matrix can consequently not be readily molded over such a bracket. It has, therefore, been suggested to secure the metal brackets with adhesive upon the model teeth before the transfer matrix is formed so that adhesive can penetrate into the perforations of the metal base and fill them. When the prepared bracket is later cemented upon teeth in the mouth, another coat of adhesive establishes at that point a bond with the teeth. However, insulation problems arise on the model teeth. The model teeth may be so well shielded by conventional insulating means that the adhesive will not adhere to the material of the model. However, the bracket does not then have the necessary holding characteristics for the production of the transfer matrix. Also, the brackets may adhere firmly on the model tooth because the insulation is less effective but in such a case layers or particles of the model material will stick to the bracket base when the matrix is lifted and they must be removed with great effort.

It has, accordingly, been attempted to affix brackets with a temporary adhesive on model teeth. It is known to use as a temporary adhesive pasty mixtures of corn flour, potato starch and water. In such cases, the temporary adhesive must be later removed completely from the brackets received in the transfer matrix. This is difficult because remnants of the temporary adhesive tend to become stuck between the matrix and the bracket base.

Additionally, in none of the known methods is it possible to take into consideration a further important condition, namely, the fact that the adhesive not only fills the perforations of the bracket bases but also covers or surrounds them in the range of the perforations and at the edges of the bases with a thin uniform layer. This also applies to plastic brackets without perforations in the bracket base. This occurs in order to insure the riveting effect necessary to hold the brackets on the teeth in the mouth. With the small dimensions of the brackets and their bases, it is practically impossible to apply the riveting adhesive layer by hand with the necessary dimension either on the model or in direct cementing of the brackets upon the teeth in the mouth.

Accordingly, it is an object of the present invention to provide a solution to the aforementioned problems whereby brackets of the type in question may be first temporarily secured upon model teeth in a simple and clean manner and may be subsequently transferred by means of the transfer matrix to the teeth in the mouth and cemented thereon.

SUMMARY OF THE INVENTION

Briefly, the present invention may be described as an orthodontic bracket assembly which comprises an orthodontic bracket including a bracket base defining a surface for fastening said bracket upon a tooth and bracket wings extending laterally from said base and defining therebetween a slot adapted to receive therein a regulating arch. The fastening surface of the base is provided with a self-adhesive layer which is adhered on one side thereof to the fastening surface of the bracket base. A protective foil is arranged between the bracket wings and the bracket base surrounding the base to the limits defined by the adhesive coat.

As a result of the configuration of the present invention, the self-adhesive layer may be easily removed after the transfer matrix is lifted from the model particularly if the self-adhesive layer consists of a double adhesive coating whose side remote from the side adhered to the bracket base is covered with a cover strip inasmuch as such a double adhesive coat can be easily removed regardless of whether the layer or coat remains on the bracket base when the transfer matrix is lifted from the model or on the model tooth. Furthermore, the protective foil ensures that the matrix material cannot settle below the bracket wings when the transfer matrix is reduced. Accordingly, harder or stiffer plastic material may be used for the matrix providing advantages for a number of reasons. Additionally, the plastic foil in a metal bracket with perforations prevents matrix material from entering the perforations.

In a metal bracket having a perforated base, it is advisable to provide the side of the protective foil facing the base of the bracket with projections in order to ensure that a spacing is provided between the side of the protective foil and the bracket base and in order also to provide an interval between the lateral edges of the bracket base and the protective foil. In this manner it is possible to facilitate introduction of adhesive through the perforations in the bracket base after the transfer matrix has been removed from the model and to distribute the adhesive above the bracket base between the base and the protective foil in order that the desired attachment effect is achieved. Additionally, the protective foil together with the transfer matrix will prevent adhesive from flowing from under the bracket wings into the bracket slot.

In a plastic bracket, the protective foil may be arranged to bear in a smooth and tight form upon the upper side of the base and an interval may be provided between the lateral edges of the base and the protective foil inasmuch as such plastic brackets have nonperforated bases and they combine chemically with sufficient strength with the adhesive. However, it is important in such a case that sufficiently adequate flow of the adhesive around the base edges is insured.

A further advantageous arrangement is obtained in accordance with the present invention if a plurality of brackets are combined by utilizing an elongated continuous protective foil strip and/or an elongated continuous self-adhesive layer having a plurality of brackets assembled therealong. Such strips can be made with different colorations, for example, in order to adapt them for use with brackets of different size and shape. The brackets may be mounted in the factory on shaped and perforated foil strips or be attached in some other way, for example, by molding the protective foil material on the bracket. Naturally, the brackets can also be provided individually with a form-locking protective foil and a self-adhesive coat.

By a further development of the present invention, a method is provided for preparing a bracket in the laboratory for application to the teeth wherein, after the bracket has been cemented with a self-adhesive coat upon the model, an elastic mold-negative or a transfer matrix of plastic foil with a modulus of elasticity of 300 $kg/cm^2$ and a wall thickness of about 0.5 to 1.0 mm is produced to receive the brackets which does not touch the gums. Such transfer matrix of harder or more rigid plastic materials makes it possible to eliminate the need that the transfer matrix cover a larger area and thus the transfer matrix need no longer extend over the adjacent gums. This is advantageous because the gums change constantly and an inaccurate fit may occur when the brackets are transferred with a gum-covering matrix to the teeth in the mouth. It is of primary importance that the application of the brackets upon the teeth in the mouth and the control of the adhesive be substantially improved due to the essentially smaller dimensions of a transfer matrix of more rigid material, particularly if the transfer matrix is cut out on the front side along the edge facing the gums and along the lateral edges close to each bracket leg. This offers easy access to the tooth surface outside the bracket base with the advantage that excess adhesive may be removed from the teeth after the transfer matrix has been inserted in the mouth before the adhesive hardens. After the adhesive has hardened, the transfer matrix can be easily removed from the teeth and from the brackets adhering thereon after which the protective foil remaining on the brackets may be easily removed, since it does not bond the adhesive when the latter is made of a correspondingly different material.

Finally, it has been found that, because of the rigid matrix material, the transfer matrix can be divided before it is used in the mouth according to tooth groups or individual teeth which further facilitates the application of the brackets upon the teeth in the mouth. A further advantage arises by virtue of the fact that frequently occurring intermediate changes in tooth positions become irrelevant with such a divided application of the brackets upon the teeth in the mouth.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAILED DESCRIPTION OF THE PREFERRED EMBODIMENTS

Figure 1:
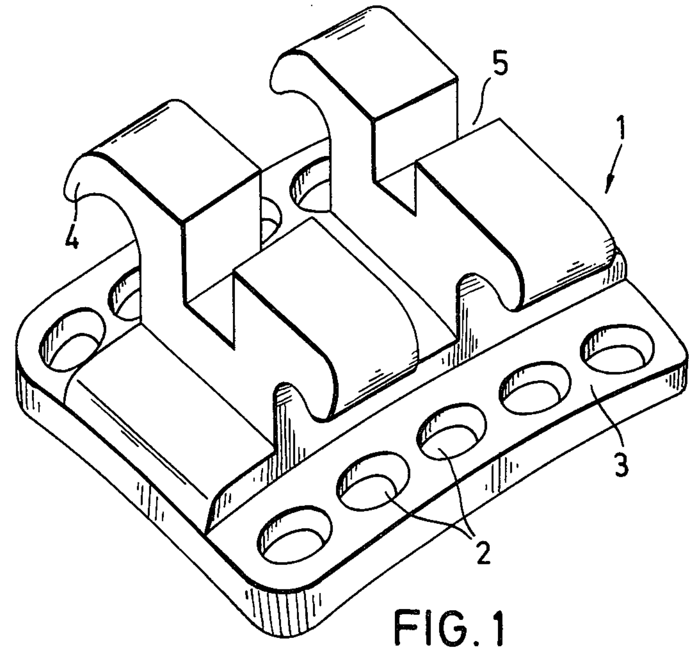
FIG. 1 is a perspective view showing a conventional metal bracket having a perforated base.
Figure 4:
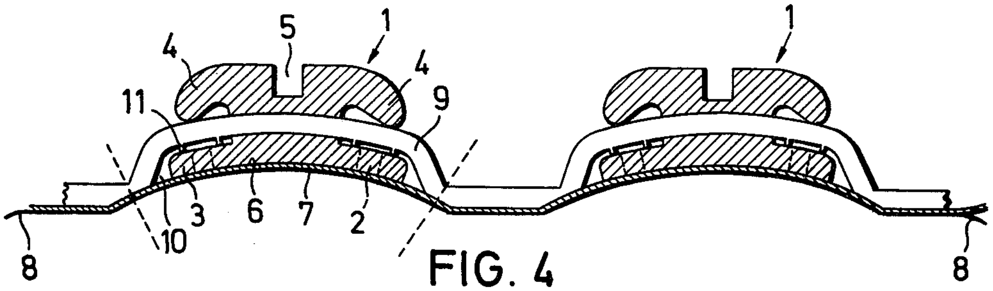
FIG. 4 is sectional view depicting a manufactured supply or assortment strip of brackets wherein a bracket assembly in accordance with the present invention is utilized.

Referring now to the drawings wherein similar reference characters are utilized to refer to similar parts throughout the various figures thereof, there is shown particularly in FIG. 4 an assortment strip of bracket assemblies in accordance with the present invention, with each of the assemblies comprising a metal bracket 1 of the type depicted in FIG. 1 having perforations 2 extending through a bracket base 3. On the upper part of the bracket 1 there are provided a plurality of bracket wings 4 adapted for fastening thereupon tightening wires and defining therethrough a central slot 5 for receiving a regulating arch. The base 3 defines on the underside thereof a fastening surface 6 which is connected or cemented with one side of a double adhesive, self-adhesive strip 7 with the opposite side of the strip 7 being covered by a cover strip 8. The self-adhesive strip or layer 7 is self-adhesive on both sides thereof.

Between the bracket base 3 and the bracket wings 4 there is provided a protective foil 9 which bears upon the bottom side of the bracket wings and which provides an interval or spacing 10 between the lateral edges of the base and one side of the protective foil 9.

Furthermore, projections 11 are provided on the underside of the protective foil 9 in the range of the bracket base thereby to ensure formation of a distance or spacing between the foil 9 and the top side of the base 3.

By combining the double adhesive strip 7 including the cover strips 8 with a protective foil 9, a number of brackets such as the bracket 1 may be formed into a supply or assortment strip each having mounted therealong a bracket assembly in accordance with the present invention. The protective foil 9 and/or the cover strip 8 of such an assortment strip may be of different colors for the purpose of coding or identifying brackets of different size or shape. When a particular bracket assembly is to be utilized, it becomes necessary merely to cut one such assembly with a single bracket, either with a pair of scissors or a sharp knife, thereby detaching the individual assembly and bracket from the assortment strip by cutting along the dotted lines represented on either side of the leftmost assembly shown in FIG. 4.

Figure 5:
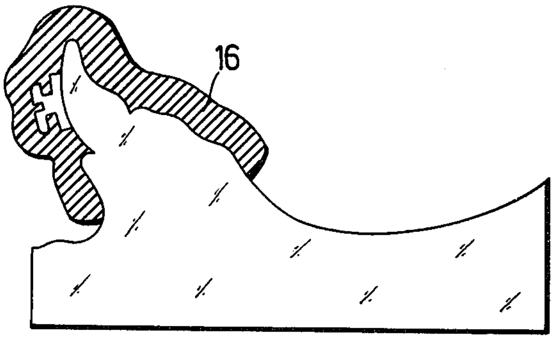
FIG. 5 is a sectional view showing a transfer matrix of a known type utilizing soft rubber and attached upon a jaw model.
Figure 6:
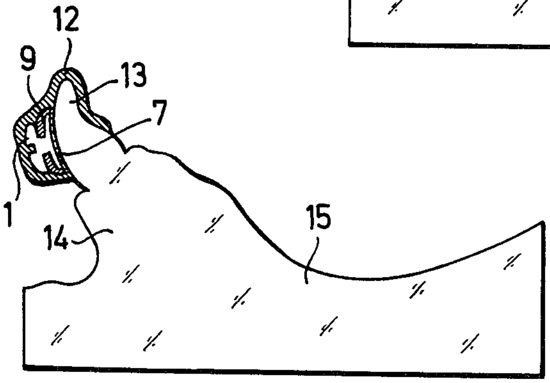
FIG. 6 is sectional view showing a transfer matrix utilizing a more rigid, thin-walled material in accordance with the present invention and likewise attached upon a jaw model.
Figure 7:
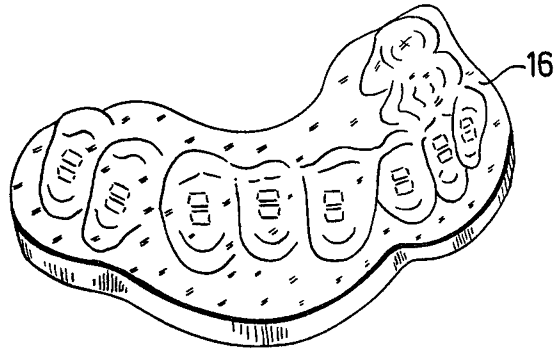
FIG. 7 shows a known transfer matrix in the finished cut state ready for insertion into the mouth.

As shown in FIG. 6, such a bracket assembly may be temporarily secured upon a model tooth 13 forming part of a positive jaw model 15 simply by removing the cover strip 8 after which a transfer matrix may be produced. The transfer matrix, of course, is produced after all of the teeth of the respective model have been applied or fitted with appropriate bracket assemblies. Such a transfer matrix may be made of a relatively rigid plastic material having a modulus of elasticity of about 300 $kg/cm^2$ and a wall thickness of between about 0.5 to 1.0 mm, as shown in FIG. 6. A comparison between the positive model shown in FIG. 6 and the model shown in FIG. 5 will indicate that, the device according to the present invention may be contrasted with a known conventional transfer matrix 16 formed of soft elastic material having a modulus of elasticity of between 700–1000 $Kg/cm^2$ and a wall thickness of 2–4 mm as shown in FIG. 5.

Furthermore, from FIG. 6 it will be seen that the transfer matrix formed in accordance with the present invention need extend over only approximately half the height of the tooth as opposed to the prior art arrangement depicted in FIG. 5.

Figure 8:
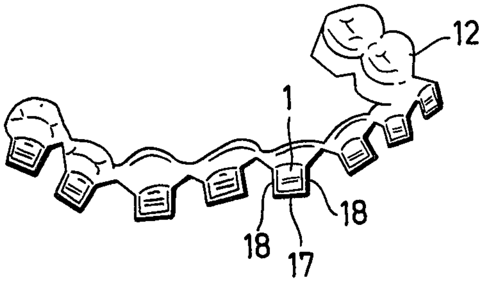
FIG. 8 shows a transfer matrix in accordance with the present invention in cut out form and ready for placement in the mouth.

Additionally, a transfer matrix 12 formed in accordance with the present invention may be cut out on the front side thereof along the edges 17 facing the gums 14 and the long two lateral edges 18 of each of the brackets, as indicated in FIG. 8. Thus, excellent accessibility is ensured when the transfer matrix is transferred into the individual teeth in the mouth. When the transfer matrix 12 is removed from the positive jaw model 15, the double self-adhesive strip 7, which is adhered between the fastening surface 6 of the bracket base 3 and the model tooth 13, is removed when transfer matrix 12 is removed. Thereafter, a suitable liquid adhesive 19 is applied on the fastening surface 6 and the adhesive flows through the perforations 2 between the protective foil 9 and the upper side of the base 3. The adhesive fills the interval between the base edges and the protective foil in such a way that the entire bracket base is surrounded by adhesive and that the desired attachment effect for the bracket base is achieved in a satisfactory manner.

Figure 2:
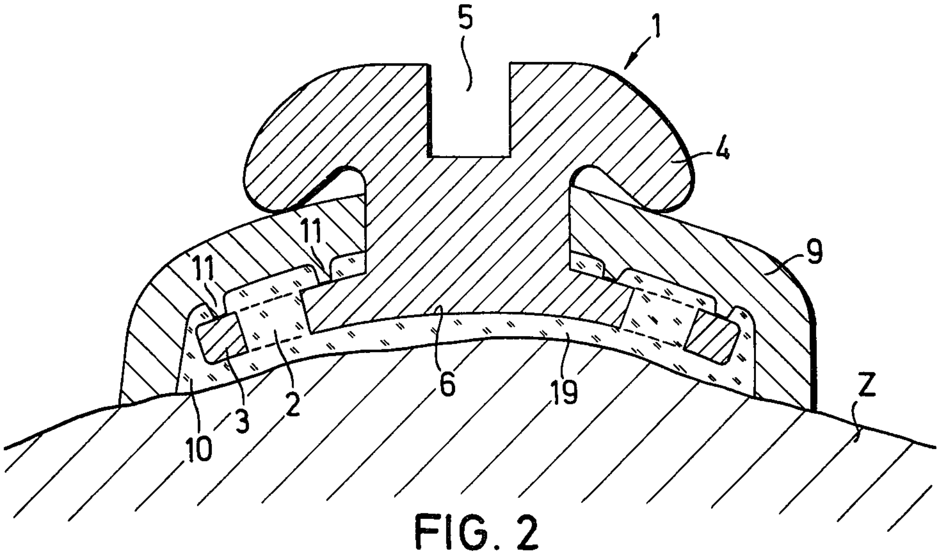
FIG. 2 is a cross sectional view showing a bracket assembly in accordance with the present invention cemented upon a tooth surface after the self-adhesive layer has been removed therefrom.

After the transfer matrix 12 has been applied upon teeth Z in the mouth, there is obtained an arrangement or position such as that indicated in FIG. 2 wherein the transfer matrix is not shown. Although the transfer matrix of this arrangement consists of a relatively more rigid material, it can nevertheless be easily removed without disturbing the position of the bracket since the transfer material, as mentioned above, does not penetrate beneath the bracket wings 4 because of the protective foil 9.

Before the bracket 1 is transferred by means of the transfer matrix 12 to the teeth Z in the mouth, the transfer matrix may be divided in such a way that groups of brackets or individual brackets are transferred to the teeth Z in the mouth. This is possible because the material of the transfer matrix, in accordance with the present invention, may be relatively rigid so that this matrix material will also ensure a sufficiently accurate and exact positioning upon the tooth even though the respective tooth is only partly covered. It will be seen that the application of the brackets upon the teeth in the mouth is thus considerably simplified and particularly other areas of the teeth not covered by the bracket base are easily accessible because of the aforementioned cutting away on the front side of the transfer matrix in order to facilitate removal of excess adhesive.

Figure 3:
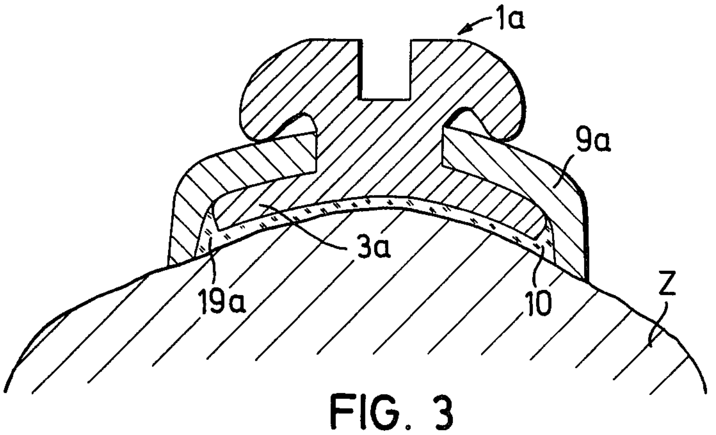
FIG. 3 is a cross sectional view in accordance with the invention showing a bracket assembly utilizing a plastic bracket cemented upon a tooth surface in a fashion similar to that shown in FIG. 2.

In a plastic bracket 1*a*, of the type represented in FIG. 3, and shown in a position corresponding to the position of the bracket of FIG. 2, the design and mode of operation are substantially the same as that utilized in connection with the metal bracket 1 which includes perforations in its bracket base 3. An exception is that the protective foil 9 provided upon the bracket 1*a* may bear smoothly on the top side of a closed bracket base 3*a* which is devoid of perforations since they are not necessary to produce the desired riveting or attachment effect in these plastic brackets due to the fact that an adhesive compatible with the material of the bracket base 3*a* may be utilized to chemically combine with the bracket base in such a way that a sufficiently strong bond is ensured.

Naturally, alternative embodiments other than the embodiments described above may be formulated without departure from the spirit and scope of the invention. For example, the brackets could also be provided individually with a protective foil and a self-adhesive strip and they could be maintained in stock in small, properly identified containers each identifying brackets of the same type. For an arrangement wherein the bracket assemblies are provided on a supplyor assortment strip, it would also be possible to pass through only the protective foil or the cover strip for the adhesive coat.

While specific embodiments of the invention have been shown and described in detail to illustrate the application of the inventive principles, it will be understood that the invention may be embodied otherwise without departing from such principles.

What is claimed is:

1. An orthodontic assembly including an orthodontic bracket which is particularly adapted for use by being first mounted with a transfer matrix upon a positive model of a tooth which is to have said bracket ultimately applied thereto after removal of said bracket from said positive model, said assembly comprising a bracket base defining on said orthodontic bracket a surface for fastening said bracket upon a tooth, bracket wings extending laterally from said base of said bracket and defining therebetween a slot adapted to receive therein a regulating arch, a self-adhesive strip removably adhered on one side thereof to said fastening surface of said bracket base and adapted to have its opposite side removably adhered to a model tooth, and a protective foil extending between said bracket wings and said bracket base and also extending to said adhesive strip in surrounding relationship with said bracket base, said protective foil being arranged to prevent penetration of the material forming said transfer matrix to the space between said bracket base and said bracket wings when said bracket is being mounted upon said positive tooth model with said transfer matrix.

2. An assembly according to claim 1 wherein said self-adhesive strip consists of a double adhesive layer having adhesive on both sides thereof and wherein said opposite side of said strip which is adapted to be removably adhered to a model tooth includes a removable cover strip extending thereover.

3. An assembly according to claim 1 wherein said bracket is made of metal with said bracket base having perforations extending therethrough, said protective foil being arranged with one side thereof facing said bracket base, said one side of said protective foil including projections extending therefrom toward said base to provide a spacing between said base and said protective foil.

4. An assembly according to claim 1 wherein said bracket is made of plastic material and wherein said protective foil extends on one side thereof in smooth abutment with said bracket base, said protective foil being configured to provide a spacing between the lateral edges of said base and said protective foil.

5. An assembly according to claim 1 wherein said self-adhesive strip is formed in an elongated configuration having a plurality of said brackets removably adhered thereto.

6. An assembly according to claim 5 wherein said plurality of brackets are arranged to form a unitary strip of said brackets consisting of brackets of different types.

7. An assembly according to claim 6 wherein said protective foil extends continuously along said strip in operative relationship with each of said plurality of brackets.

8. An assembly according to claim 1 further comprising a model tooth having said opposite side of said self-adhesive strip adhered thereto, and a transfer matrix adapted to enable said assembly to be transferred from said model tooth to a tooth to be orthodontically treated thereby, said transfer matrix being composed of plastic material having a modulus of elasticity of about 3000 $Kg/cm^2$ and a wall thickness of between about 0.5 to 1.0 mm.

9. An assembly according to claim 8 including a positive jaw model having said model tooth formed as part thereof and including gum portions from which said model tooth extends, said transfer matrix being formed on said model tooth so as to avoid contact thereof with said gum portions.

10. An assembly according to claim 9 wherein said transfer matrix includes a front side along an edge thereof facing said gums and two lateral edges close to said bracket base, said transfer matrix being cut out on said front side and along said two lateral edges 11. An assembly according to claim 10 wherein said transfer matrix is subdivided prior to being utilized upon teeth to be orthodontically treated according to groups of individual teeth.

* * * * *